United States Patent [19]

Geary et al.

[11] 4,151,272

[45] Apr. 24, 1979

[54] WAX-LIKE ANTIPERSPIRANT STICK COMPOSITIONS

[75] Inventors: Daniel C. Geary, Randolph, N.J.; Helga Krevald, Tarrytown, N.Y.

[73] Assignee: American Cyanamid Company, Stamford, Conn.

[21] Appl. No.: 869,077

[22] Filed: Jan. 13, 1978

Related U.S. Application Data

[63] Continuation-in-part of Ser. No. 710,951, Aug. 2, 1976, abandoned.

[51] Int. Cl.$^2$ .................... A61K 7/34; A61K 7/36; A61K 7/38
[52] U.S. Cl. .................... 424/68; 424/DIG. 5; 424/66; 424/67; 424/357
[58] Field of Search .................... 424/65, 68, DIG. 5, 424/66, 67

[56] References Cited

U.S. PATENT DOCUMENTS

| 2,617,754 | 11/1952 | Neely | 424/DIG. 5 |
| 3,300,387 | 11/1967 | Kale | 424/68 |
| 3,324,004 | 6/1967 | Nagler | 424/68 |

FOREIGN PATENT DOCUMENTS

| 2241030 | 3/1973 | Fed. Rep. of Germany | 424/47 |
| 2365219 | 12/1973 | Fed. Rep. of Germany | 424/68 |
| 2442314 | 3/1975 | Fed. Rep. of Germany | 424/47 |
| 844769 | 9/1961 | France | 424/66 |
| 7103689 | 9/1971 | Netherlands | 424/47 |

*Primary Examiner*—Dale R. Ore
*Attorney, Agent, or Firm*—Charles J. Fickey

[57] ABSTRACT

Wax-like compositions useful for antiperspirant or deodorant sticks, generally hydrophobic in nature, which contain ingredients having a high hydrophile-lipophile balance to improve the efficacy of such compositions.

12 Claims, No Drawings

WAX-LIKE ANTIPERSPIRANT STICK COMPOSITIONS

This application is a continuation-in-part of our previous application Ser. No. 710,951, filed Aug. 2, 1976, now abandoned.

This invention relates to improvements in bases useful for cosmetic and pharmaceutical preparations in general, and to antiperspirant and deodorant compositions in particular. More specifically, the invention relates to wax-like compositions useful for antiperspirant or deodorant sticks, generally hydrophobic in nature, which contain ingredients having a high hydrophile-lipophile balance (HLB) to improve the efficacy of such compositions.

In general, both cosmetic and pharmaceutical preparations in the form of sticks consist of wax-like components, usually hydrophobic in nature, which function mainly as a base for an active ingredient. In the case of antiperspirants the active ingredient is normally an astringent, such as aluminum chlorohydrate, or another similarly used compound. The wax-base may, of course, consist of many ingredients to provide specific properties in addition to its primary function.

British Pat. No. 1,156,812 describes a cosmetic or pharmaceutical stick in which the base consists of mixtures of polyglycol esters of fatty acids, for example $C_{12}$ to $C_{22}$ fatty acids, such as stearic acid, and polyglycol esters of wax acids, such as Montanic wax. The patentees additionally disclose that fatty alcohols, such as stearyl alcohol, may be incorporated as well as certain ingredients that care for the skin or improve the absorbability of the active ingredient.

The polyglycol esters of fatty acids and wax acids are obtained by esterification thereof with alkylene oxides or polyethylene glycols, built up from 2 to 100, preferably 3 to 30 molecules of ethylene oxide. Thus, the esters have the structure:

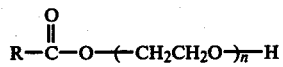

wherein R represents the aliphatic portion of the alcohol and n is an integer from 2 to 100.

We have now discovered that the efficacy of cosmetic and pharmaceutical preparations containing an active ingredient, particularly antiperspirant compositions containing an astringent, is greatly enhanced if the wax-like, generally hydrophobic bases used therein contain polyetherified fatty alcohol of the formula:

wherein R represents the aliphatic portion of a fatty alcohol of 12 to 22 carbon atoms, preferably 16 to 18 carbon atoms, and n is an integer of from about 100 to about 200.

Aluminum chlorhydrate and aluminum-zirconium hydroxy chloride and many other active astringent compounds show good antiperspirant efficacy using recognized efficacy testing protocols when applied as a solution to humans.

When these same active compounds are incorporated into antiperspirant sticks containing stearyl alcohols at levels of 15–30%, the stearyl alcohol coats the active particles. Since the stearyl alcohol and any other fatty alcohol are oil loving in nature, they prevent the water of perspiration from dissolving the particles of active astringent to the extent that these particles are coated.

Naturally the efficacy that is achieved is dependent on the ratio of stearyl alcohol and active material present. If sufficient stearyl alcohol is present to form a mono molecular film on every particle of active material, no antiperspirant efficacy will be observed. More important than the weight/weight ratio of stearyl alcohol to active material, is the ratio of the weight of the stearyl alcohol necessary to form the mono molecular film to the total surface area of the active material.

Our invention insures that persons obtain good efficacy from antiperspirant sticks. It has been discovered that highly ethoxylated fatty alcohols, 100, 150 and 200 moles of ethylene oxide per mole of fatty alcohol, can be dispersed throughout the stearyl alcohol to provide a discontinuous film. Whereever the highly ethoxylated fatty alcohol is located in the film, water of perspiration can pass through the oil loving film and dissolve the active astringent material. It has been found that 1% of stearyl alcohol (ethoxylated with 100 moles ethyleneoxide) is sufficient to provide a sufficiently discontinuous film to allow the water soluble active materials to be dissolved. Higher ethoxylated fatty alcohols function (i.e. with 150 and 200 moles ethylene oxide) in the same manner. This would also be true of similar compounds such as cetyl alcohol or stearates which are ethoxylated to the same extent.

Since, it is desired to limit the active astringent to about 25% and we further keep the level of fatty alcohol to a minimum, sufficient only to form a stick, another ingredient is added to reach 100% by weight. Cyclic silicones, not linear silicones, have been chosen to make up the difference. Cyclic silicones were chosen because they are volatile. They exist as a liquid dispersed throught the solid stick. It takes 10 to 20 hours, depending on the choice of volatile silicone for all of the volatile silicone to volatilize. If the volatile silicone did not volatilize, it would remain coated around the active particles like the fatty alcohol and prevent the water of perspiration from dissolving the actives.

It is desired to obtain a deposit on the skin where the amount of fatty material present is less than the active material. With the use of volatile cyclic silicones, this has been found to be 1:2 to 1:1.25. With conventional sticks not having a cyclic silicone, the ratio is from 2:1 to 3:1.

Overall, the invention lies in depositing a discontinuous thin film of product composed of fatty alcohols, volatile silicone and highly ethoxylated material through which the water of perspiration can reach the active astringent material. This is further aided by the volatilization of the cyclic silicones with time. The fact that 10 to 20 hours is required for the silicones to volatilize is not a hinderance since it takes at least 12 hours for even water solution active astringents to provide maximum efficacy.

We have found from efficacy tests that formulations that include 1% added stearyl alcohol (ethoxylated with 100 moles of ethylene oxide) show 30% more sweat reduction than sticks with stearyl alcohol and volatile silicone alone, each containing 25% aluminum chlorhydrate. Even greater differences are possible with higher ratios of the polyethoxylated fatty alcohols to fatty alcohols are utilized. But aesthetics of the stick are also equally important. No matter how efficacious the stick, it would not be appealing to the consumer if aesthetically unacceptable.

We have found that the bases generally used heretofore in antiperspirant compositions, especially those containing aluminum chlorohydrate, form a hydrophobic film around the aluminum chlorohydroxide, thus preventing or at least interferring with permeation of moisture (perspiration) through the film, which is necessary in order to activate the aluminum chlorohydroxide or other astringent and thereby provide effective antiperspirant activity. The bases generally used heretofore, including those described in British Pat. No. 1,156,812, that is, the preferred compositions containing polyethoxylated esters having 3 to 20 moles of ethylene oxide, have not adequately overcome this problem and are therefor not entirely satisfactory in providing high antiperspirant efficacy.

The polyetherified fatty alcohols of the present invention, however, facilitate moisture permeation through the film surrounding the active ingredient, thereby enhancing contact thereof with the axilla, and increasing the efficacy of the antiperspirant composition.

The polyetherified fatty alcohols useful in the present invention, as described by the aforementioned formula, are obtained by the condensation of from about 100 to 200 moles of ethylene oxide with a fatty alcohol containing from about 12 to 22 carbon atoms, preferably 16 to 18 carbon atoms. Polyethoxylated stearyl alcohol, cetyl alcohol, or mixtures thereof, are preferred. In addition, other polyethoxylated (100 to 200 moles of ethylene oxide) materials may be used such as fatty acids; straight or branched chain fatty esters (including unsaturated chains), e.g. methyl, ethyl and isopropyl stearate and isopropyl oleate; di-, tri-, and polycarboxylic fatty acids or esters; fatty diols, triols and polyols; and fatty chains containing a combination of one or more hydroxyl or carboxylic groups, all of said materials having from 12 to 22 carbon atoms in the fatty chain.

The polymers obtained by etherification of the fatty alcohols appear to exhibit a high hydrophile-lipophile balance heretofore not known or used in cosmetic preparations. Polyethoxylated lower alcohols, for example polyethoxylated butyl alcohol, containing up to about 50-60 molecules of ethylene oxide are known and are available on the market.

The polyetherified fatty alcohols may also be obtained by etherification of a fatty alcohol with a polymer of ethylene oxide.

Hydrophile-lipophile balance (HLB) is a term well known to cosmetic chemists, and was first suggested by Griffen, J. Soc. Cosmetic Chemists 1,311 (1949).

The amount of polyetherified fatty alcohol used in the compositions of the present invention may range from about 0.01 to 5.0 percent by weight, preferably about 1.0 to 3.0 percent by weight.

The antiperspirant compositions of the present invention may comprise a fatty alcohol base, such as stearyl alcohol or cetyl alcohol or mixture thereof; a polyethoxylated fatty alcohol, such as polyethoxylated stearyl or cetyl alcohol, or mixture thereof, containing from about 100 to 200 moles of ethylene oxide per mole of said fatty alcohol; an astringent material and a volatile silicone. Alternatively, the fatty alcohol may be replaced in part, depending on the hardness of the stick desired, with up to about 5 percent by weight of a modified clay, such as a montmorillonite clay, for example the Bentones (National Lead Ind.), which are reaction products of the clay with dimethyl distearyl ammonium chloride; or, all of the fatty alcohol may be replaced with the ethoxylated fatty alcohol and the hardness adjusted with the Bentones. In any case, no more than about 5 percent by weight of the Bentones should be used. It should be emphasized, however, that as the ethylene oxide content of the ethoxylated fatty alcohol increases the hardness of the product will increase also.

We have also found that antiperspirant compositions containing a volatile silicone provide improved non-staining properties and are non-sticky. Silicones volatile under the conditions of use which may be used are, certain cyclic silicones, which are oligomers of dimethyl siloxane, are preferred. Examples of such silicones include the methyl tetramer, pentamers and hexamer (I) and (II), and (III), respectively.

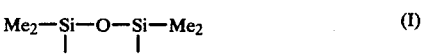

2,4,6,8-octamethylcyclotetrasiloxane

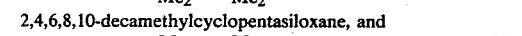

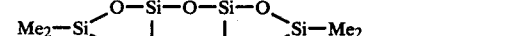

2,4,6,8,10-decamethylcyclopentasiloxane, and

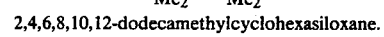
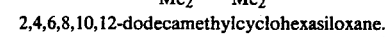
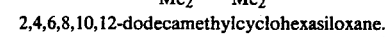

2,4,6,8,10,12-dodecamethylcyclohexasiloxane.

The cyclic silicones are isolated from the hydrolysis product of dimethyldichlorosilane; see Patnode, Wilcock, J. Am. Chem. Soc. 68, 358 (1946). The cyclic volatile silicone, may be used in an amount up to about 80 percent by weight.

Among the useful astringents are aluminum sulfate, aluminum chloride, aluminum chlorohydrate, aluminum sulfocarbolate, aluminum-zirconium chlorhydrate, zinc chloride, zinc sulfocarbolate, zinc sulfate, zirconium salts, such as zirconium chlorohydrate, combinations of aluminum chloride and aluminum-zirconium chlorhydrate, aluminum-zirconium chlorhydroglycine and the like. In the aluminum chlorhydrate, and aluminum-zirconium chlorhydrate, the ratio of aluminum to chloride may range from 2.1:1 to 0.9:1 and the ratio of aluminum to zirconium may range from 2.5:1 to 10.5:1. Aluminum chlorhydrate is preferred. It may be used as a solution or in granular or impalpable form.

The astringent material may also be suspended or dissolved in water or alcohol. Where the astringent is suspended in the stick, a Bentone, such as Bentone 27, 34, or 38 may be used to improve the suspension and provide a more homogeneous dispersion. Where the astringent is predissolved in water or alcohol, a fumed silica (hydrophobic) such as TULLANOX (Cabot, Inc.) may be added in a suitable blender to form a dry powder form of the astringent which may be added to the stick.

The active ingredient may be used in amounts up to about 35% by weight, although normally from about 15 to 25% by weight is used. In any case, sufficient should be added to provide a 20% reduction in perspiration in 50% of the population. More astringent is usually needed in a stick form of antiperspirant.

The sticks of the present invention containing about 25% aluminum chlorohydrate are also excellent deodorants.

The following examples further illustrate the invention.

EXAMPLE 1

|  | Parts by Weight |
|---|---|
| Ethoxylated stearyl alcohol (1) | 1.0 |
| Stearyl alcohol (95%) | 20.0 |
| Aluminum chlorohydrate | 25.0 |
| Aluminum chloride hexahydrate (50% aqueous solution) | 4.0 |
| Fumed silica (2) | 0.2 |
| Cyclic silicone pentamer (3) | 49.2 |
| Fragrance | 0.6 |
|  | 100.0 |

(1) $CH_3(CH_2)_{17}O\text{-}(CH_2CH_2O)_{200}H$
(2) Silane treated, hydrophobic, Tullanox 500, Cabot, Inc.
(3) 2,4,6,8,10-decamethylcyclopentasiloxane Stearyl alcohol, ethoxylated stearyl alcohol and the cyclic silicone are melted together at 65° C. and kept agitated. The aluminum chlorohydrate and the aluminum chloride mixed with the fumed silica are added at 65° C. and stirred until homogeneously dispersed. Finally, the fragrance is added and the batch passed through an in-line shear flow pump at 65° C. (at least one pass is required). The batch is then allowed to cool to 52°–55° C., poured into suitable containers and then cooled to 40° C.

The ethoxylated stearyl alcohol in the above formulation may be replaced by stearyl alcohol ethoxylated with 150 or 200 moles of ethylene oxide, or with a similarly ethoxylated cetyl alcohol, with similar results.

EXAMPLE 2

|  | Parts by Weight |
|---|---|
| Ethoxylated Stearyl alcohol (1) | 1.0 |
| Stearyl Alcohol (95%) | 20.0 |
| Aluminum chlorohydrate (4) | 25.0 |
| Bentone 38 | 0.5 |
| Montan Wax | 1.0 |
| Cyclic silicone pentamer | 51.9 |
| Fragrance | 0.6 |
|  | 100.0 |

(4) Organically treated to be alcohol soluble.

EXAMPLE 3

|  | Parts by Weight |
|---|---|
| Ethoxylated stearyl alcohol (1) | 1.0 |
| Stearyl alcohol (95%) | 20.0 |
| Aluminum/Zirconium chlorohydrate | 29.0 |
| Fumed silica (2) | 0.2 |
| Cyclic silicone pentamer (3) | 49.2 |
| Fragrance | 0.6 |
|  | 100.0 |

EXAMPLE 4

|  | Parts by Weight |
|---|---|
| Ethoxylated cetyl alcohol (5) | 1.0 |
| Cetyl alcohol | 17.0 |
| Aluminum chlorohydrate | 15.0 |
| Aluminum chlorohydroxide (50% aqueous solution) | 20.0 |
| Fumed silica | 1.0 |
| Cyclic silicone tetramer (6) | 45.4 |
| Fragrance | 0.6 |
|  | 100.0 |

(5) $CH_3(CH_2)_{14}CH_2O\text{-}(CH_2CH_2O)_{100}H$
(6) 1,3,5,7-octamethylcyclotetrasiloxane

EXAMPLE 5

|  | Parts by Weight |
|---|---|
| Ethoxylated stearyl alcohol (1) | 1.0 |
| Stearyl alcohol (95%) | 20.0 |
| Aluminum chlorohydrate | 25.0 |
| Bentonite clay (7) | 0.5 |
| Cyclic silicone pentamer | 52.9 |
| Fragrance | 0.6 |
|  | 100.0 |

(7) Organically treated Montmorillonite clay.

EXAMPLE 6

|  | Parts by Weight |
|---|---|
| Ethoxylated stearyl alcohol (1) | 1.0 |
| Stearyl alcohol (95%) | 20.0 |
| Aluminum chloride hexahydrate (50% aqueous solution) | 4.0 |
| Fumed silica | 0.2 |
| Cyclic silicone pentamer | 74.2 |
| Fragrance | 0.6 |
|  | 100.0 |

EXAMPLE 7

|  | Parts by Weight |
|---|---|
| Ethoxylated stearyl alcohol (8) | 1.0 |
| Stearyl alcohol (95%) | 20.0 |
| Aluminum chlorohydrate (50% aqueous solution) | 16.0 |
| Aluminum chloride hexahydrate (50% aqueous solution) | 4.0 |
| Fumed silica | 1.0 |
| Aluminum chlorohydroxide | 15.0 |
| Cyclic silicone pentamer | 42.4 |
| Fragrance | 0.6 |
|  | 100.0 |

(8) $CH_3(CH_2)_{17}O\text{-}(CH_2CH_2O)_{200}H$

EXAMPLE 8

|  | Parts by Weight |
|---|---|
| Ethoxylated Stearyl Alcohol | 1.0 |
| Stearyl Alcohol (95%) | 20.0 |
| Aluminum chlorhydrate | 25.0 |
| Cyclic Silicone Pentamer | 53.4 |
| Fragrance | 0.6 |
|  | 100.0 |

We claim:

1. An antiperspirant stick consisting essentially of from about 15 to 30% by weight of a wax-like fatty alcohol, from about 15 to 35% by weight of an astringent material, in an amount up to about 80% by weight of a volatile silicone, from about 0.01 to 5% by weight of a polyethoxylated fatty alcohol represented by the formula:

$$R-O-(CH_2CH_2O)_{\overline{n}}H$$

wherein R represents an alkyl radical of about 16 to 18 carbon atoms and n is an integer of about 100 to 200.

2. An antiperspirant stick according to claim 1 wherein said astringent material is aluminum chlorohydrate.

3. An antiperspirant stick according to claim 1 wherein said volatile silicone is selected from the group consisting of 2,4,6,8-octamethylcyclotetrasiloxane, 2,4,6,8,10-decamethylcyclopentasiloxane, and 2,4,6,8,10,12-dodecamethylcyclohexasiloxane.

4. An antiperspirant stick according to claim 1 wherein R is selected from the group consisting of stearyl, cetyl and mixtures thereof, and n is 100.

5. An antiperspirant stick according to claim 1 wherein R is selected from the group consisting of stearyl, cetyl and mixtures thereof, and n is 150.

6. An antiperspirant stick according to claim 1 wherein R is selected from the group consisting of stearyl, cetyl and mixtures thereof, and n is 200.

7. An antiperspirant stick according to claim 1 wherein said wax-like fatty alcohol is stearyl alcohol.

8. An antiperspirant stick according to claim 1 wherein said wax-like fatty alcohol is cetyl alcohol.

9. An antiperspirant according to claim 1 comprising up to 5 percent by weight of a modified clay obtained by reacting a bentonite or hectorite clay with dimethyldistearylammonium chloride.

10. An antiperspirant stick according to claim 1 wherein said polyethoxylated fatty alcohol comprises from about 0.1 to 5% by weight.

11. An antiperspirant stick consisting essentially of from about 15 to 30% by weight of stearyl alcohol or cetyl alcohol, or mixtures thereof, from about 15 to 35% weight of aluminum chlorohydroxide, up to 80% by weight of a volatile silicone, and from about 0.01 to 5% by weight a polyethoxylated fatty alcohol represented by the formula:

$$R-O-(CH_2CH_2O)_{\overline{n}}H$$

wherein R represents an alkyl radical of about 16 to 18 carbon atoms and n is an integer from about 100 to 200.

12. An antiperspirant stick according to claim 1 containing fumed silica.

* * * * *